United States Patent [19]

Saunders

[11] Patent Number: 5,334,134
[45] Date of Patent: Aug. 2, 1994

[54] LUMBOSACRAL BACK SUPPORT RELEASABLY SECURED TO A STABILIZING BELT

[75] Inventor: Harold D. Saunders, Eden Prairie, Minn.

[73] Assignee: The Saunders Group, Chaska, Minn.

[21] Appl. No.: 984,343

[22] Filed: Dec. 2, 1992

Related U.S. Application Data

[63] Continuation-in-part of Ser. No. 719,267, Jun. 21, 1991, Pat. No. 5,205,815.

[51] Int. Cl.⁵ .................................. A61F 5/00
[52] U.S. Cl. ................................ 602/19; 450/112; 128/100.1
[58] Field of Search .............. 602/19; 128/96.1, 100.1, 128/101.1; 450/94, 95, 110, 112, 121, 144, 154; 2/44

[56] References Cited

U.S. PATENT DOCUMENTS

| | | |
|---|---|---|
| 94,087 | 8/1869 | Dike ................... 602/19 X |
| 1,599,688 | 9/1926 | Sullivan . |
| 2,088,302 | 7/1937 | McKeever . |
| 2,232,246 | 2/1941 | Klein . |
| 2,249,198 | 7/1941 | Carter . |
| 2,481,396 | 9/1949 | Cohen . |
| 2,553,353 | 5/1951 | Binder et al. . |
| 2,641,258 | 6/1953 | Rutledge . |
| 2,910,984 | 11/1959 | Yeakey et al. . |
| 3,029,814 | 4/1962 | Kravitz . |
| 3,141,457 | 7/1964 | Davidson . |
| 3,234,937 | 2/1966 | Nelkin . |
| 3,441,027 | 4/1969 | Lehman . |
| 3,454,003 | 7/1969 | Sailhen . |
| 3,526,229 | 9/1970 | Blair . |
| 3,756,247 | 9/1973 | Hand . |
| 3,920,008 | 11/1975 | Lehman . |
| 4,175,553 | 11/1979 | Rosenberg ............ 602/19 |
| 4,400,832 | 8/1983 | Kinder . |
| 4,475,543 | 10/1984 | Brooks et al. . |
| 4,572,167 | 2/1986 | Brunswick ............ 602/19 |
| 4,833,730 | 5/1989 | Nelson ................ 2/44 |
| 4,836,194 | 6/1989 | Sebastian et al. ...... 602/19 |
| 4,907,576 | 3/1990 | Curlee ................ 602/19 |
| 4,941,237 | 7/1990 | Hovis . |
| 4,947,870 | 8/1990 | Larcher .............. 602/19 X |
| 5,040,524 | 8/1991 | Votel et al. . |
| 5,086,759 | 2/1992 | Buddingh ............. 602/19 |
| 5,111,806 | 5/1992 | Travis ................ 602/19 |
| 5,122,111 | 6/1992 | Sebastian et al. ...... 602/19 |
| 5,147,261 | 9/1992 | Smith et al. .......... 602/19 X |
| 5,148,549 | 9/1992 | Sydor ................ 602/19 X |
| 5,188,586 | 2/1993 | Castel et al. . |

FOREIGN PATENT DOCUMENTS

| | | |
|---|---|---|
| 0410904 | 1/1991 | European Pat. Off. ...... 602/19 |
| 1290920 | 3/1962 | France . |
| 2243787 | 11/1991 | United Kingdom . |

OTHER PUBLICATIONS

*Managing Lower Back Pain*, 2d Ed., W. H. Kirkaldy-Willis, Churchill Livingstone, 1988, pp. 297–303.
*Camp Therapy Products Price List*, Camp International, Inc., Jun. 1988.
News release article on the Dyna-Life ™ Active Support Belt.
Saunders Therapy Products catalog, p. 26, 27, 28 and 35.

Primary Examiner—Richard J. Apley
Assistant Examiner—Linda C. M. Dvorak
Attorney, Agent, or Firm—Schwegman, Lundberg & Woessner

[57] ABSTRACT

A lumbosacral back support member is releasably secured to the user by a stabilizing belt generally worn over the user's clothes. The stabilizing belt may be inserted into the belt loops on the user's pants, attached to the belt loops, or engaged with the narrow portion of the user's waist. The lumbosacral support member is releasable attached to the stabilizing belt. The user positions the lumbosacral support member around the spine from approximately the sacrum to at least the L3 lumbar vertebra.

19 Claims, 5 Drawing Sheets

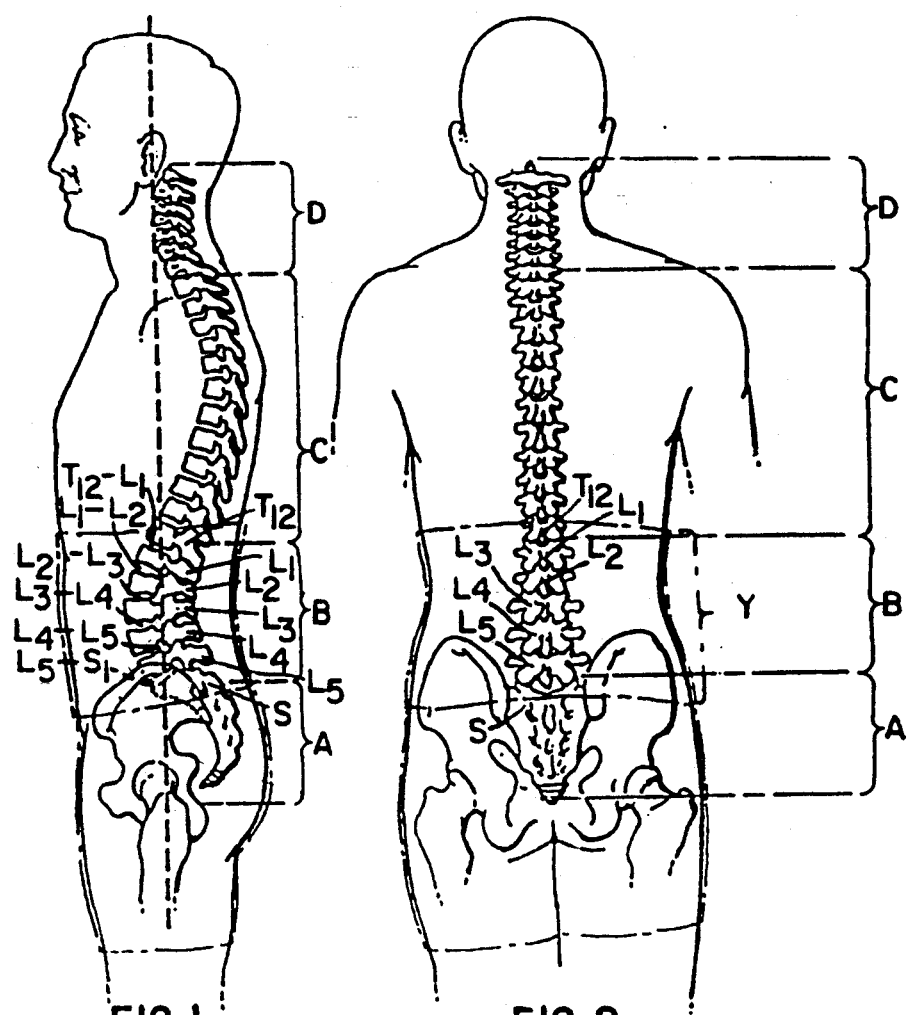
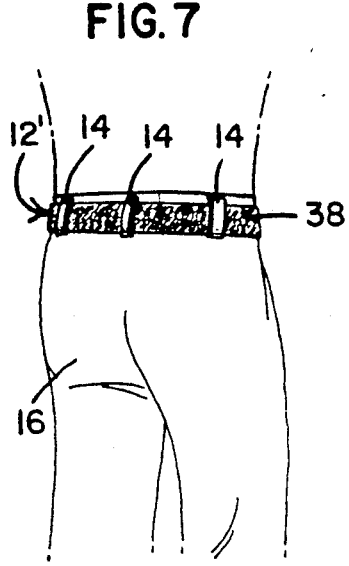
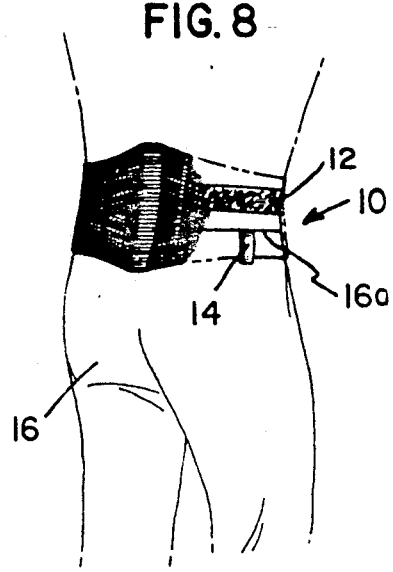
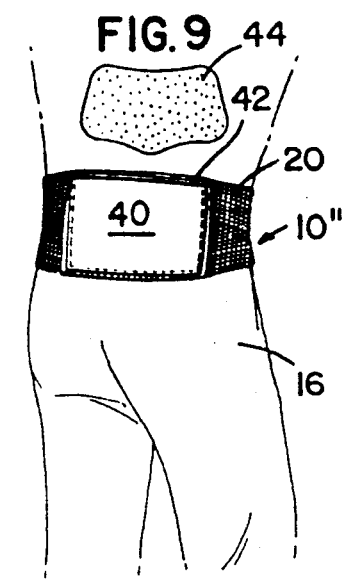

LUMBOSACRAL BACK SUPPORT RELEASABLY SECURED TO A STABILIZING BELT

This application is a continuation-in-part of application Ser. No. 07/719,267, entitled ATHLETIC BACK SUPPORT APPARATUS, filed Jun. 21, 1991, now U.S. Pat. No. 5,205,815.

BACKGROUND OF THE INVENTION

1. Field of the Invention

This invention relates generally to a lumbosacral back support system for medical or industrial applications, and more specifically, to a lumbosacral support member releasably secured to the user by a stabilizing belt which is generally worn over, or as a part of, the user's clothes.

2. Description of the Art

Lower back disorders and the pain associated therewith have become epidemic in today's society. Such disorders are typically caused by a combination of poor posture, faulty body mechanics, stressful living and working habits, loss of flexibility and a general decline in physical fitness. In general, the best non-surgical management techniques for such disorders include proper strengthening exercises, treatment and rest, and back-care education. However, there are many instances in which orthopedic devices or orthoses in the form of lumbosacral braces or supports can be effectively used to supplement such management techniques or to help prevent injury or re-injury to the lower back. Orthotic devices are particularly useful in reducing mobility of the spine joints so as to reduce the amount of intervertebral bending and intervertebral torsion in the regions where the back support is applied. Orthotic devices also function to lessen the average axial loading and bending loading on the spine, thereby avoiding or reducing strain and aggravation to the spine during physical activity. Such orthoses (typically referred to as "back-braces" or "back supports") devices are also helpful in reminding the wearer of the fact that an injury has taken place and that he should not make sudden motions that will override the protective mechanisms of his body. Finally, orthopedic devices provide protection against rapid dynamic motions that occur during strenuous industrial work or repetitious activity.

Prior orthotic devices lack the versatility to accommodate a wide range of patient needs. These devices tend to be rigidly structured to provide a particular level of support at a fixed location. However, each patient will have different needs with regard to the level and location of support required from the orthotic device. The required level of support may also vary with the particular activity performed. Additionally, the need for a particular level and/or location of support may change over time for an individual patient. Therefore, the ideal orthopedic treatment may require a variety of orthotic devices for a particular patient. However, having to substitute different orthotic devices over the course of treatment is extremely costly and inconvenient to the patient.

A variety of lower back support orthoses have been developed. Such devices, which are typically configured to provide sacroiliac support or support for the lumbar spine region, have generally been effective for use by those who do not have to regularly adjust or remove the support device.

The need for orthotic devices is particularly acute for those involved in industrial work activities or repetitive tasks which place abnormal stress and strain on the spine or office work that requires sitting for an extended period. However, industrial workers or office workers often need the option to affix, remove or adjust the orthotic device on short notice. Since most orthotic devices are worn under clothing, the user must disrobe to make adjustments or remove the device, rendering such devices impractical for industrial or office applications. The unfortunate consequence is the workers tend to not wear support devices when required. For example, workers may only need to wear the orthotic device for brief periods or need to adjust the level of support quickly. In performing their required functions, such individuals do not always have the opportunity to observe desired back safety and protection guidelines and often need the additional support and protection provided by an orthopedic orthosis.

Prior devices worn over the clothes, which may be adjusted or removed, have a tendency to migrate or ride up on the body of the wearer. Since it is estimated that 90% of back injuries occur in the lower two vertebra of the lumbar portion of the spine, it is essential that the back support be securely attached to the user during use. Support migration or riding-up is aggravated when the worker engages in bending, stretching, or twisting. Even sitting for prolonged periods can cause these devices to ride up. In particular, prior devices necessarily partially encircle the pelvis and hips and at least partially overlie the upper buttocks region of the wearer. This configuration naturally tends to urge the orthosis upward on the body during physical activity. On an active wearer, it does not take long for such orthosis to rapidly migrate upward on the body, thereby decreasing its effectiveness and becoming very uncomfortable for the wearer. In such instances, the orthosis becomes more of an impediment to the wearer than an aid.

Efforts have been made in the art to maintain the desired position of the orthosis on the body. Crotch, groin and leg straps secured to the lower edges of the orthotic device have been used in an attempt to keep the device from riding up on the wearer's body. Shoulder straps are often used to prevent the orthotic device from moving downward on the patient during times of inactivity.

Such retaining structures, however, have been largely unacceptable to active wearers such as industrial or office workers, due to the appearance and discomfort. These retaining structures also make it extremely inconvenient and time consuming for the user to affix, remove or adjust the orthotic device to their body. Because of the inconvenience and appearance of retaining structures of prior art devices, users are often left with the option of wearing the orthotic device for extended periods, even when not required, or not wearing it at all.

The present invention provides a lumbosacral support member which is releasably secured to the user by a stabilizing belt generally worn as an ordinary belt, or strap incorporated within and releasably secured to the belt loops of the user's clothes, or over the user's clothes, allowing the support member to be easily adjusted or removed. These strap configurations prevent the support from moving out of location during use.

SUMMARY OF THE INVENTION

The present invention relates to a lumbosacral back support member which is releasably secured to the user by a stabilizing belt or strap generally worn over the user's clothes.

In the first embodiment of the present invention, a stabilizing belt or strap is attached to the belt loops on the user's pants. The stabilizing belt has a first releasable attachment mechanism on its outer surface. The lumbosacral support member has a second releasable attachment mechanism on its inner surface for engagement with the first attachment mechanism on the stabilizing belt. The user positions the lumbosacral support member around the spine from approximately the sacrum to at least the L3 lumbar vertebra. The first and second releasable attachment mechanisms automatically engage to retain the lumbosacral support member to a fixed location on the user's spine.

The lumbosacral support member may optionally have a third attachment mechanism on its outer surface for receiving a supplemental lumbosacral support member. A supplemental lumbosacral support member having a fourth releasable attachment mechanism on its inner surface may then be placed around the primary lumbosacral support member to provide additional support as required.

In an alternate embodiment, the stabilizing belt may be attached to the user's waist over his or her clothes. The stabilizing belt is preferably attached to the narrowest portion of the user's waist, thereby minimizing movement. Again, the lumbosacral support member is positioned around the user's waist and secured into place. The corresponding first and second releasable attachment mechanisms engage to retain the lumbosacral support member to the user's spine.

The method of the present invention involves attaching the stabilizing belt to the user's waist, either around the narrow portion of the waist or attaching it to the loops on the user's pants. The lumbosacral support member is then positioned around the user's waist to engage the spine from approximately the sacrum to at least the L3 lumbar vertebra. The first and second releasable attachment mechanisms operate to releasably retain the support member accurately to the user's spine, even during physical activity.

BRIEF DESCRIPTION OF THE DRAWINGS

Referring to the drawings, wherein like numerals represent like parts throughout the several views:

FIG. 1 is a diagrammatic side view representation of a human body illustrating the four defined physiological curve regions of the spine;

FIG. 2 is a diagrammatic representation of the human body of FIG. 1, illustrated from a back or posterior view;

FIG. 7 is a back view illustrating a preferred stabilizing belt engaged with the belt loops on the user's pants;

FIG. 8 is an alternate method of using the first preferred back support system whereby the stabilizing belt is attached to the narrow portion of the user's waist;

FIG. 9 is a back perspective view of an alternate embodiment of the preferred back support system modified to include an insertable thermoform moldable insert.

DETAILED DESCRIPTION OF THE PREFERRED EMBODIMENT

Figure 3:
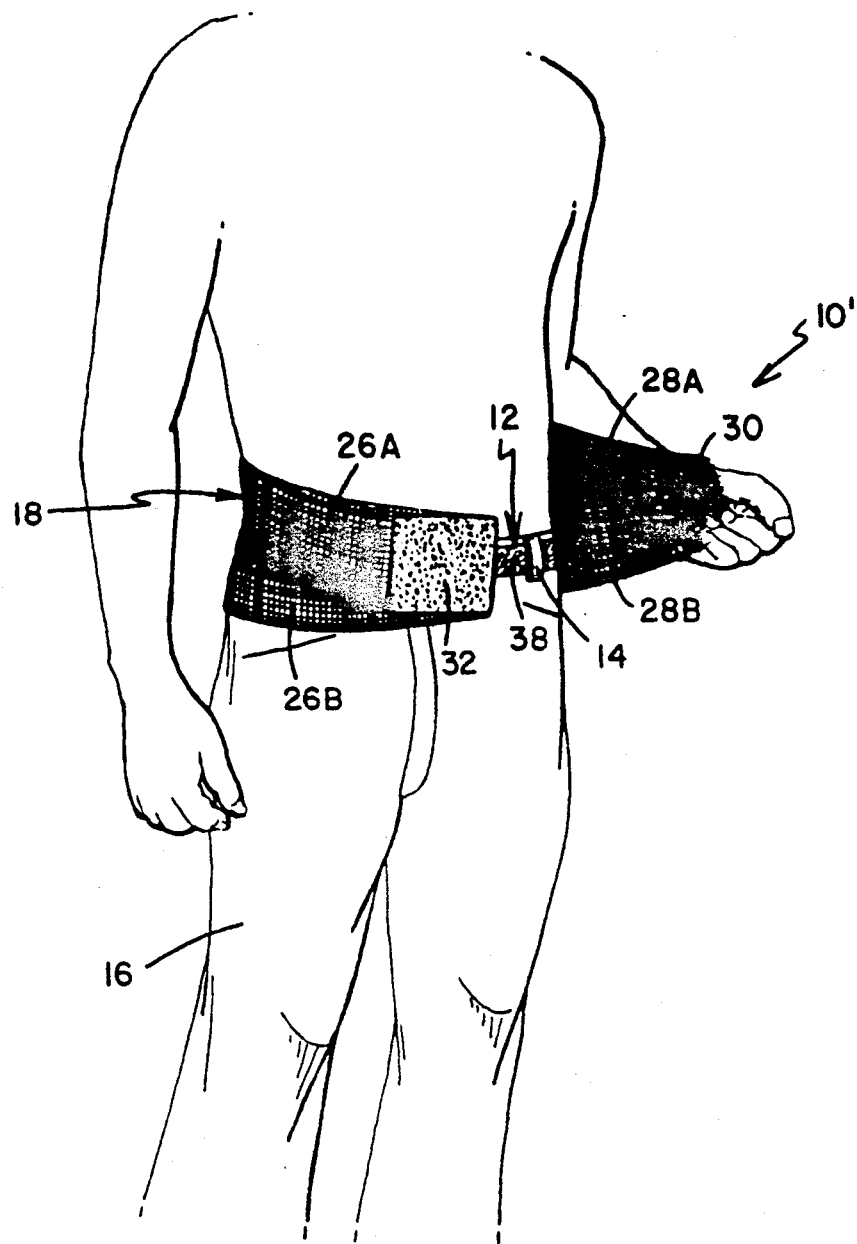
FIG. 3 is a front perspective view of a first preferred embodiment of a lumbosacral back support system of the present invention illustrated as it would be operatively positioned on a human body.

Diagrammatic views of a human body, generally illustrating the spinal column and its orientation and position relative to the sacrum and ilium of the sacroiliac region of the body are illustrated in FIGS. 1 and 2. FIGS. 1 and 2 will be used to facilitate describing placement of the lumbosacral back support system of this invention relative to the human body and to the vertebrae of the spinal column. It is not the intent of this specification to describe the operation of the spine or medical disorders associated with the spinal column. Those skilled in the art are knowledgeable in such matters and/or need not be knowledgeable in the physiological peculiarities of the human body in order to effectively use the present invention. For a more detailed description, however, of the physiological anatomy of the spinal column and of the various musculoskeletal disorders associated therewith, the reader is referred to the text *Evaluation, Treatment and Prevention of Musculoskeletal Disorders* by H. Duane Saunders, Educational Opportunities, 1985. To the extent that any of the materials of my above-identified book are relevant to an understanding of the art, or of the use or applicability of my invention to providing support for the spinal vertebrae of the human body, they are herein incorporated by reference.

In general, with reference to FIGS. 1 and 2, the spine has four curved areas generally designated at "A, B, C and D". The sacral curved region "A" comprising the fused bones of the sacrum is convex posteriorly. The lumbar region of the spine, generally designated at "B" is concave posteriorly. The thoracic region of the spine "C" is convex posteriorly. The cervical region of the spine, generally designated at "D" is concave posteriorly. This invention focuses primarily in providing support for those portions "A" and "B" of the spinal column referred to as the lumbosacral region. The lumbar region generally includes five vertebrae generally labeled "$L_1$" through "$L_5$" in FIGS. 1 and 2. The $L_5$ lowermost vertebra of the lumbar region lies adjacent the sacrum "S" and is separated thereby by spinal joint labeled "$L_5$-$S_1$" The uppermost vertebra "$L_1$" of the lumbar region lies adjacent to and is separated from the lowermost vertebra "$T_{12}$" of the thoracic region by the joint labeled as "$T_{12}$-$L_1$". While there is some dispute as to the relative percentages of lumbar flexion/extension of the various joints in the lumbar region, most authorities agree that most of the flexion/extension takes place at the "$L_4$-$L_5$" and the "$L_5$-$S_1$" joints.

It will be understood by those skilled in the art that the lumbosacral back support system of the present invention may also be referred to as a lumbar support orthosis. As will be discussed in detail below, the lumbosacral support system of the present invention may consist of a number of components. In the preferred embodiment, these components are generally at least one lumbosacral support member releasably attached to a stabilizing belt. The specification discloses two alternative lumbosacral support members, referred to as either a support strap assembly or back support band. It will be understood by those skilled in the art that a variety of lumbosacral support member configurations are suitable for the claimed invention.

The lumbosacral back support system preferably includes one or more stay members, which distribute pressure throughout the lumbosacral spine region of the user. The lumbosacral back support system may also include a removable insert member to provide additional support.

The preferred embodiments are constructed to enable the lumbosacral support member to be worn over the clothes of the user while being accurately aligned with the user's body, thereby maximizing the degree of immobilization of the lumbar vertebrae. Further, the lumbosacral support members may be easily removed and replaced with alternate support members, or repositioned to a location more suited to the user's needs. Finally, the entire lumbosacral back support system is constructed of appropriate materials and is designed so as to maximize comfort to the wearer, even during vigorous physical activity, while achieving its functional purposes.

Referring to FIG. 3, the first embodiment of a lumbosacral back support system 10 configured according to the principles of the present invention are illustrated. The lumbosacral back support system 10 preferably comprises a stabilizing belt 12 inserted into the belt loops 14 on the user's pants 16. A lumbosacral support assembly 18 is releasably attached to the stabilizing belt 12, as will be discussed below. The stabilizing belt 12 may also operate as an ordinary belt. It will be understood that the stabilizing belt 12 may also be attached directly to the belt loops on the user's pants, without being inserted into the loops 14. For example, the stabilizing belt 12 may include hooks for engagement with either the pants loops or the user's belt.

Figure 4:
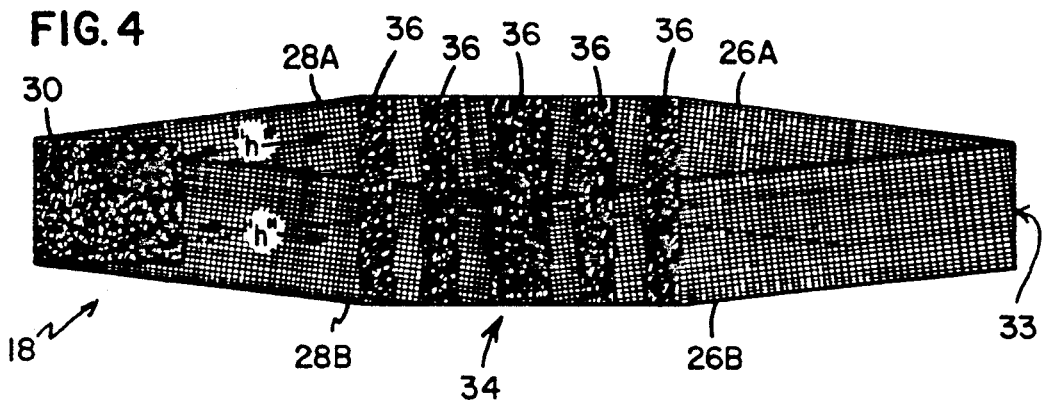
FIG. 4 illustrates the inside surface of the first preferred lumbosacral support assembly which may be attached to the stabilizing belt of FIG. 7.

FIG. 4 illustrates the preferred lumbosacral support assembly 18, including adjustable support straps 26, 28 joined to form a single unit. Support straps 28A, 28B are tapered as they proceed from the square center portion 34 toward a hook panel 30. The free ends of the support straps 26A and 26B are joined at intersection 33. The square center portion 34 of the straps 26, 28 is preferably constructed of an elastic material, while the tapered end portions may be constructed of an inelastic cloth material. The individual support straps 26A, 26B and 28A, 28B may alternatively be constructed of relatively stiff elastic material which is elastic primarily only in the direction as indicated by the arrows "h".

The inside surface of the lumbosacral support assembly 18 is designed to be releasably attached to the stabilizing belt 12. Preferably, loop portions 36 of a hook-and-loop fastener mechanism is attached to a plurality of locations on the inside surface of the lumbosacral support assembly 18. Alternatively, separate adjustable support straps having suitably located Velcro ® may be overlapped with one another to form a lumbosacral support assembly 18 illustrated in FIG. 4.

Now turning to FIG. 3, the adjustable support straps 26 and 28 taper from the posterior of the lumbosacral back support system toward their free ends and overlap one another. As discussed above, the end portion of the support strap 28 includes a panel of hook fastener material 30 on the inside surface. The end portion of the support straps 26A and 26B includes a panel of looped fastener material 32 secured to its outer surface for engagement with the hook panel 30. The support strap assembly 18 is connected proximate to the user's spine by engaging the Velcro ® hook fastener material 30 on the support strap 28 to the looped fastener material 32 on the strap 26.

The preferred stabilizing belt 12 containing hook portion 38, illustrated in FIG. 7, is preferably inserted into belt loops 14 on the user's pants. As discussed above, the belt 12 may be directly attached to the belt loops 14, without being inserted through the loops. Although a variety of attachment mechanisms are possible, such as snaps, looped portion 36 and hooked portion 38 constructed of Velcro ® are preferred.

It will be appreciated that the loop 36 and hook 38 portions of the releasable Velcro ® attachment mechanism do not have to be in complete alignment to provide adequate attachment force between the support assembly 18 and the stabilizing belt 12. Further, the relative size of the loop 36 and hook 38 portions provides additional flexibility for locating the support assembly 18 relative to the stabilizing belt 12.

The releasable attachment mechanism 36, 38 on the support strap assembly 18 allows the user to locate the support strap assembly 18 at the ideal location for his or her orthopedic needs. Further, the ease with which the support strap assembly 18 is removed allows the user to quickly substitute an alternate support strap assembly without having to remove any clothing. The ability to interchange the support strap assemblies 18 or adjust the location of the support strap assembly 18 relative to the user's spine allows the lumbosacral back support system of the present invention to satisfy the changing needs of an individual user.

The method of the first embodiment of the present invention requires the user to attach the stabilizing belt 12 to the belt loops 14 on his/her pants 16. While FIG. 7 illustrates the stabilizing belt 12 inserted into the belt loops 14, it will be understood that it may be attached to the belt loops 14 by a number of different methods. The support strap assembly 18 is then aligned with the wearer's spinal column by engaging the hook fastener 30 with the loop panel 32. By doing so, the lumbosacral vertebrae and joints of the wearer are supported. Once secured, the loop portion 36 on the support strap 18 automatically engages with the hook portion 38 on the stabilizing belt 12.

Due to the strength of the releasable attachment mechanism 36 and 38, the adjustable support straps 26, 28 are securely fixed at the desired support position on the user. The interchangeable and positionally adjustable nature of the adjustable support straps 26 and 28 enable the degree of immobilization support provided to the spinal column and the amount of support provided to the abdomen to be varied according to the needs of the user. The support assembly 18 may also be easily removed when not needed.

In an alternate method of use, illustrated in FIG. 8, the stabilizing belt 12 may be secured to the user's waist over clothing. Preferably, the belt 12 is located at the narrowest portion of the waist, to minimize the chance of movement. The narrowest portion is usually just above the top 16a of the pants 16. The support strap assembly 18 is then positioned to the desired location and the hook and loop fastener 30, 32 on the support strap assembly 18 are engaged. The loop and hook fasteners 36, 38 on the stabilizing belt 12 and support strap 18 will automatically engage to secure the support strap assembly 18 to the user.

Figure 5:
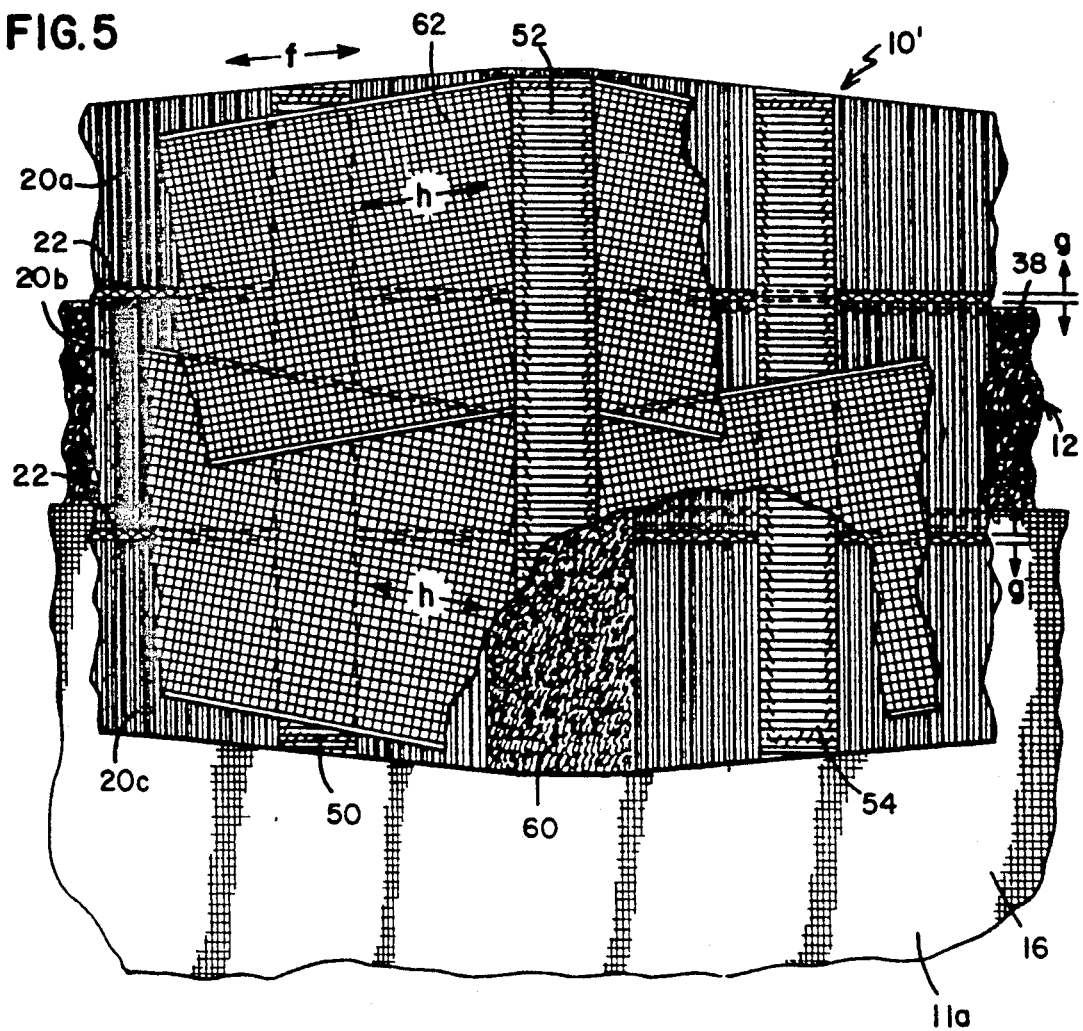
FIG. 5 is an enlarged fragmentary view with sections thereof broken away of the back portion of a second preferred lumbosacral back support band and supplemental support member.
Figure 6:
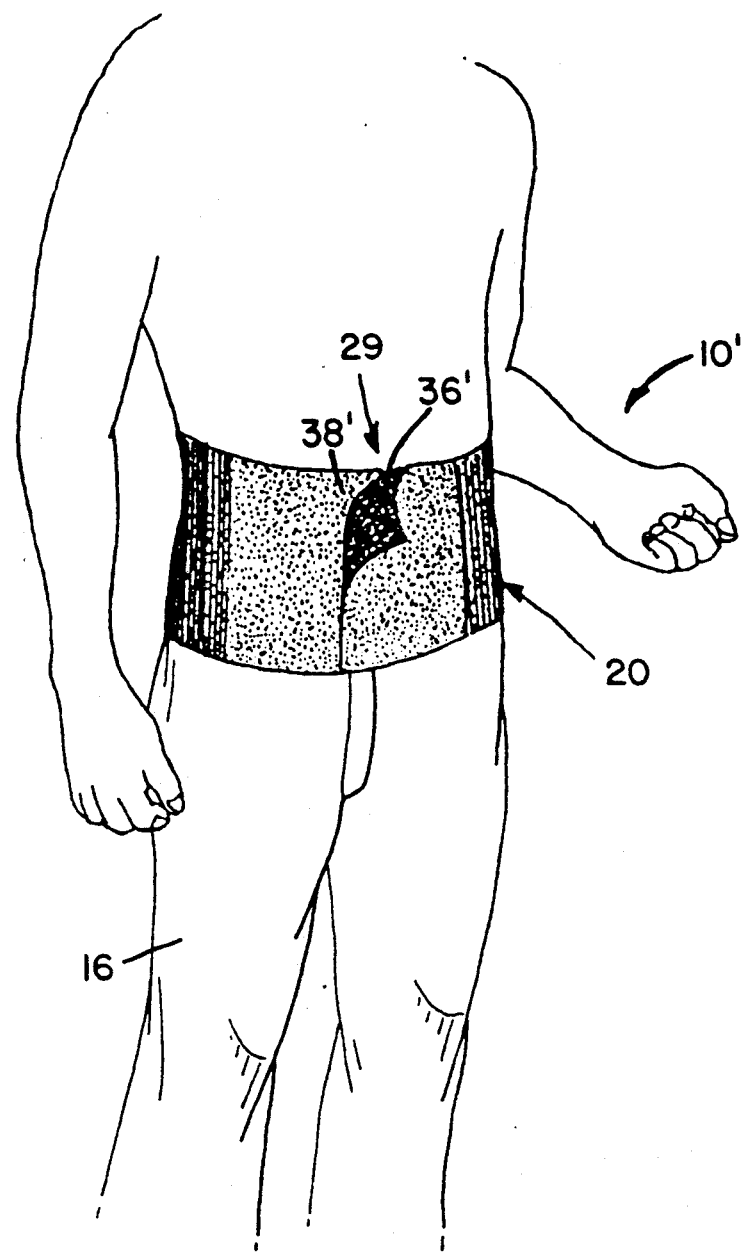
FIG. 6 is a front perspective view of the second preferred embodiment of the lumbosacral back support system with an adjustable back support band.

In a second embodiment, an elastic circumferential back support band 20 may be substituted for the support strap assembly 18, as best illustrated in FIGS. 5 and 6. FIG. 5 also illustrates an optional supplemental lumbosacral support member 62 attached to the outside of the back support band 20, which will be discussed in detail below.

FIG. 6 shows the back support band 20 engaged to the user's waist, without the supplemental support member 62 of FIG. 5. The back support band 20 is provided with a vertical split 29 along the front portion thereof for adjusting the pressure provided by the back support band 20. The ends of the elastic back support band 20 proximate the vertical split 29 are preferably detachably secured to one another by the loop fastener 36' and hook panel 38' discussed above.

The back support band 20 in FIG. 5 preferably comprises a single piece of heavyweight elastic material with elasticity preferably running only in the directions of the arrow "f". Alternatively, the support band 20 may be constructed as three individual support bands 20a, 20b and 20c, circumferentially joined by cross-stitching 22 along their respective adjacent edges. The individual support bands 20a, 20b and 20c may be of the same or different circumferential lengths.

The cross-stitching 22 between the multiple bands 20a, 20b and 20c provides limited inter-band elasticity in the direction indicated by the arrows "g" to enable the multiple-band configuration to more readily conform to the body contours of the wearer. It will be understood by those skilled in the art that the particular construction of the back support band 20 is not to be limited to that herein described for the preferred embodiment. For example, while a multiple-band configuration comprising three interconnected bands has been illustrated, any number of such bands or strips of material comprising a multiple-band configuration could be employed to better conform to the body of the user.

The inside surface of the back support band 20 contains a plurality of panels of loop material 36 (not shown) for engagement with the hook portion 38 on the stabilizing belt 12, similar to the construction discussed in connection with FIG. 3. A plurality of flexible stay members 50, 52 and 54 are preferably securely attached in generally vertical alignment in circumferentially spaced positions along the posterior portion of the back support band 20. While FIG. 5 illustrates the flexible stay members 50, 52, and 54 all of the same length, it will be recognized that different length stays may be preferable for particular users. Alternatively, the flexible stay members 50, 52, and 54 may be attached to the adjustable support straps 26 and 28 of the support assembly 18, discussed in FIG. 4.

In the second preferred embodiment illustrated in FIG. 5, the central stay member 52 may be operatively positioned for direct vertical alignment with the spinal column of the wearer, and the stay members 50 and 54 are configured so as to be vertically aligned slightly to either side of the spinal column. The length of the stay members generally corresponds to the width or height of the back support band 20. It will be understood by those skilled in the art, however, that there need not be an identical correspondence in such dimensions and that the number and relative spacing of such stay members may vary. The length of the stay members 50, 52, 54 and their relative operative position with respect to the vertebrae of the spinal column of the wearer may be the same as previously discussed with respect to the width or height dimensions of the back support band 20 and their positioning relative to the spinal column of the user. The stay members are preferably constructed of any appropriate semi-rigid material such as plastic or metal. Alternatively, the stays are made from hardened, galvanized spring steel round wire which is coiled and flattened, generally referred to as "spiral boning". Such materials provides support rigidity for partially immobilizing the spinal column vertebrae, yet can be flexed, when placed under pressure, to conform to the body contours of the wearer.

The adjustable back support band 20 enables the user to adjust the pressure on flexible stays 50, 52, 54 and the degree of compression around the user's waist. The pressure from the back support band 20 bring the stays 50, 52 and 54 into firm engagement with the user's back. When thus secured, the stay members 50, 52, and 54, serve to partially immobilize the motion of the lumbosacral vertebrae, thereby reducing the amount of interspine bending and interspine torsion in such regions and decreases the pressures acting on the intervertebral disks. The elastic nature of the preferred circumferential back support band 20 also provide abdominal support.

In yet another alternate embodiment, also illustrated in FIG. 5, the first and second embodiments discussed above may include an additional panel of hook material 60 on the outside surface of the lumbosacral support member 18, 20 for receiving a supplemental lumbosacral support member 62. It will be understood that the use of the supplemental support member 62 may also be combined with the support assembly 18.

The supplemental lumbosacral support member 62 is designed to provide additional support by surrounding the basic support members 18, 20. It will also be understood that as an alternative to using the supplemental support member 62, different lumbosacral support members 18, 20 may be easily substituted to provide the required level of support.

The supplemental support member 62 is preferably constructed similar to the support strap assembly illustrated in FIG. 4, although it will be understood that a variety of lumbosacral support members may be used. It will also be understood that a supplemental lumbosacral support member 62 may be used in combination with any of the embodiments disclosed herein.

Figure 10:
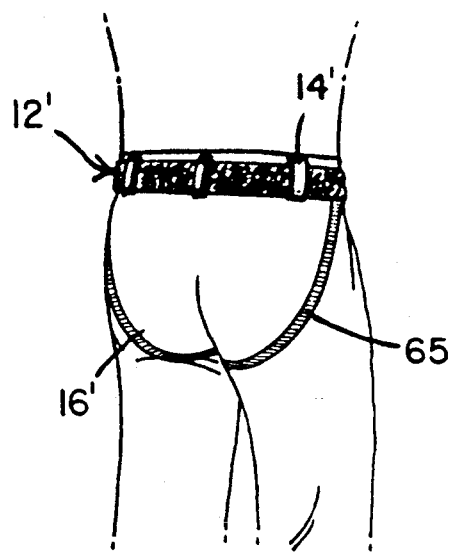
FIG. 10 illustrates the use of leg straps to further secure the stabilizing belt to the waist of the user.

FIG. 10 illustrates yet another embodiment of the present invention whereby stabilizing belt 12' is further secured to the user by leg straps 65 worn over the user's pants. The leg straps 65 preferably pass through the user's crotch region to prevent the stabilizing belt 12' from moving vertically upward on the user. It will be understood that the leg straps 65 may be used whether or not the stabilizing belt 12' has been inserted into the user's belt loops 14' of the pants 16'.

The height or width of the lumbosacral support members 18, 20 can vary, depending upon the size of the user or the orthopedic requirements. For an adult, the support member's width or height is preferably between 8 and 12 inches. More important, however, than the height or width dimensions of the lumbosacral support members 18 and 20 is their location in relation to the spine of the user. With reference to FIGS. 1 and 2, the support members 18 and 20 should preferably be designed to extend on the wearer such that its lower edge extends to the sacrum and even more preferably to the middle of the sacrum, and such that its upper edge at least covers the first two joints (L$_4$-L$_5$ and L$_3$-L$_4$) of the lumbar region. More preferably still, the upper edge should extend so as to cover all five vertebrae and all of the intervening joints of the lumbar region, as illustrated by the region "y" in FIG. 2.

A number of additional features may be added, and changes made to either of the above-described embodiments. An example of one such additional feature is diagrammatically illustrated in FIG. 9. Referring thereto, the lumbosacral back support system 10" may be modified to include a pocket or pouch 40 attached to the "inside" surface of the support strap assembly 18 or back support band 20. The pocket 40 may be oriented so as to address the lumbosacral region of the wearer's spine and may be positioned between the lumbosacral support members 18, 20 and the stabilizing belt 12.

The pocket 40 has an upper access port 42 that may accommodate appropriate closure means and is sized and configured to cooperatively accept a thermoform moldable insert member 44. Insert 44 is illustrated in FIG. 9, removed from the pocket 40. Such insert members generally have an inner core of thermoplastic material having a peripheral shape that conforms to the general contour of the lower back, and an outer coating of foam padding or other material to enhance wearer comfort. Upon application of heat, the thermoplastic of the insert becomes pliable and can be molded to the desired orthotic shape that uniquely "fits" the lumbosacral back region of the wearer. Upon cooling, the insert retains its molded shape. While such inserts can assume any desired size and shape, in the preferred embodiment the insert has a "width" that spans virtually the entire back area of the wearer and a "height" that is approximately the same as that of the lumbosacral back support members 18, 20.

It will be appreciated that the preferred lumbosacral back support systems provide the combined benefits of a back support band with the convenience of being interchangeable and positionally adjustable without having to remove clothing. The releasable attachment mechanism used to attach the lumbosacral support members 18, 20 to the stabilizing belt 12 provides sufficient stability of the lumbosacral back support system 10 so that the user can engage in active movement. The preferred embodiments provide for versatile alignment, adjustment or substitution of the primary lumbar support portions of the lumbosacral back support system.

While the present invention has been described with respect to its use for medical and industrial applications, it will be understood that the invention is not to be so limited, but can be used by any individual requiring or desiring the combined support features offered by this invention.

While the preferred embodiments are described with respect to particular brands and types of materials, it will be understood by those skilled in the art that the invention is not to be limited by any particular type or brand of material, but that such materials are used for descriptive purposes only. Further, while the invention will be described with respect to a particular style of lumbar support orthosis using a particular number and style and configuration of vertical stay members, it will be understood by those skilled in the art that the invention is not limited, other than as claimed, to the particulars of the orthosis structures described in the preferred embodiments. Further, while the present invention will be described with respect to a lumbosacral back support system which has a primary function of providing support for the lumbar spine region, it will be understood that additional support structures such as those specifically developed for sacroiliac support could be incorporated within the overall structure of the lumbosacral back support system. These and other modifications and applications of the invention will become apparent to those skilled in the art in light of the following description of preferred embodiments of this invention.

Other modifications of the invention will be apparent to those skilled in the art in view of the foregoing descriptions. These descriptions are intended to provide specific examples of embodiments which clearly disclose the present invention. Accordingly, the invention is not limited to the described embodiments or to the use of specific elements, dimensions, materials or configurations contained therein. All alternative modifications and variations of the present invention which fall within the spirit and broad scope of the appended claims are covered.

What is claimed is:

1. A lumbosacral back support system for releasably securing a lumbosacral back support to the spine of a user proximate the user's waist, the user wearing a lower body garment, comprising:
   a lower body garment having a waist portion with belt loops located proximate the waist portion;
   stabilizing belt means for insertion through the belt loops, the stabilizing belt means having an inner and outer surface with first releasable attachment means located on the outer surface so that the first releasable attachment means face away from the user; and
   at least one lumbosacral support member having an inner and outer surface with second releasable attachment means on the inner surface for automatically engaging with the first releasable attachment means when the lumbosacral support member is brought into contact with the stabilizing belt means, the first and second releasable attachment means being arranged so that the lumbosacral support member engages the user's spine from approximately the sacrum to at least the L$_3$ lumbar vertebrae, whereby the stabilizing belt means maintains the vertical position of the lumbosacral support member relative to the spine of the user during active movement.

2. The apparatus of claim 1 wherein the second releasable attachment means is located at a plurality of locations on the inner surface of the support member.

3. The apparatus of claim 1, wherein the lumbosacral support member comprises at least one adjustable strap member having a first end, middle portion, second end, and fastening means attached to the first end and the second end for adjustably closing the adjustable strap member around the user's spine.

4. The apparatus of claim 3 wherein at least the middle portion of the adjustable strap member is constructed of an elastic material.

5. The apparatus of claim 1 wherein the first and second attachment means are a hook and loop material.

6. The apparatus of claim 1, wherein the lumbosacral support member has a third attachment means on the outer surface for receiving a supplemental lumbosacral support member.

7. The apparatus of claim 6 further including a supplemental lumbosacral support member having an inner and outer surface with fourth releasable attachment means on the inner surface thereof for engaging with the third releasable attachment means on the lumbosacral support member, the third and fourth releasable attachment means arranged so that the supplemental lumbosacral support member generally surrounds the lumbosacral support member.

8. The apparatus of claim 1, wherein the lumbosacral support member comprises a plurality of interconnected circumferential bands arranged for supporting the lumbosacral spine region of the user.

9. The apparatus of claim 1 wherein the lumbosacral support member includes at least one semi-flexible stay member for supporting the lumbosacral spine region of the user.

10. The apparatus of claim 9, further including aligning means for orienting the stay member generally parallel to an axis defined by the lumbar vertebrae on the user's spine.

11. The apparatus of claim 9, wherein the stay member is configured to engage the user's spine from approximately the sacrum to at least the $L_3$ lumbar vertebra of the user's spine.

12. The apparatus of claim 1, wherein the lumbosacral support member includes means for releasably retaining a formable insert brace member proximate the lumbosacral region, the formable insert being formed to uniquely conform to the shape of the user's spine.

13. The apparatus of claim 12 wherein the means for releasably retaining the formable insert comprises a pocket on the support member.

14. A lumbosacral back support system for releasably securing a lumbosacral back support to the spine of a user proximate the user's waist, the user wearing a lower body garment, comprising:
    a lower body garment having a waist portion with belt loops located proximate the waist portion;
    a stabilizing belt for insertion through the user's belt loops, the belt having an inner and outer surface with first releasable attachment means located on the outer surface so that the first releasable attachment means faces away from the user;
    a circumferentially discontinuous back support band having an inner and outer surface extending circumferentially around the body of the user, the inner surface having second attachment means for automatically releasably connecting the back support band to the stabilizing belt when the support band is brought into contact with the stabilizing belt so that the stabilizing belt maintains the vertical position of the support band relative to the spine of the user during active movement, the back support band having at least a portion thereof configured to supportively engage the lumbosacral spine region of the user's spine; and
    fastener means attached to the support band proximate the discontinuity for adjustably closing the support band discontinuity around the waist of the user.

15. The apparatus of claim 14, wherein the support band comprises a plurality of interconnected circumferential bands arranged to conform to the contours of the user's body.

16. The apparatus of claim 14, further including at least one semi-flexible stay member operatively attached to the support band for supporting the lumbosacral spine region of the user.

17. A method for using a lumbosacral back support system for releasably securing a lumbosacral back support to the spine of a user during physical activity, the user wearing pants with belt loops, comprising:
    providing a stabilizing belt having an inner and outer surface with first releasable attachment means located on the outer surface thereof;
    inserting the stabilizing belt through the user's belt loops so that the first releasable attachment means faces away from the user;
    providing at least one lumbosacral support member having an inner and outer surface with second releasable attachment means on the inner surface for automatically engaging with the first releasable attachment means when the support member is brought into contact with the stabilizing belt means; and
    positioning the lumbosacral support member to automatically engage the first and second attachment means so that the lumbosacral support engages the user's spine from approximately the sacrum to at lest the $L_3$ lumbar vertebrae, whereby the stabilizing belt maintains the vertical position of the lumbosacral support member relative to the user during physical activity.

18. The method of claim 17 further including the steps of:
    providing a third releasable attachment means on the outer surface of the lumbosacral support member for receiving a supplemental lumbosacral support member;
    providing a supplemental lumbosacral support member having an inner and outer surface with fourth releasable attachment means on the inner surface thereof; and
    positioning the supplemental lumbosacral support member so that the third and fourth releasable attachment means engage and the supplemental lumbosacral support member generally surrounds the lumbosacral support member.

19. The method of claim 17 further including the step of removing the lumbosacral support member from the stabilizing belt means when the physical activity is completed.

* * * * *